United States Patent
Lang

[11] Patent Number: 6,030,409
[45] Date of Patent: Feb. 29, 2000

[54] MEDICAL FORCEPS

[76] Inventor: Dieter Lang, Wolfersdorfer Strasse 14, D-96342 Stockheim, Germany

[21] Appl. No.: 09/307,054

[22] Filed: May 7, 1999

Related U.S. Application Data

[63] Continuation of application No. PCT/EP97/06215, Nov. 8, 1997.

[51] Int. Cl.[7] .................................................. A61B 17/28
[52] U.S. Cl. ........................... 606/205; 606/207; 606/206
[58] Field of Search .................................. 606/205, 207, 606/174, 172

[56] References Cited

U.S. PATENT DOCUMENTS

| | | |
|---|---|---|
| 4,243,047 | 1/1981 | Olsen . |
| 4,711,240 | 12/1987 | Goldwasser et al. . |
| 4,919,152 | 4/1990 | Ger . |
| 5,250,072 | 10/1993 | Jain ........................................ 606/205 |
| 5,800,449 | 9/1998 | Wales ..................................... 606/172 |
| 5,810,865 | 9/1998 | Koscher et al. ........................ 606/174 |

FOREIGN PATENT DOCUMENTS

| | | |
|---|---|---|
| 0598607A1 | 5/1994 | European Pat. Off. . |
| 4100219A1 | 7/1992 | Germany . |
| 196 46 326A1 | 5/1998 | Germany . |

OTHER PUBLICATIONS

Brochure for "Storz. die Welt der Endoskopie," 3 pages—Jan. 1994.

*Primary Examiner*—Michael Buiz
*Assistant Examiner*—Anthony S. King
*Attorney, Agent, or Firm*—St. Onge Steward Johnston & Reens LLC

[57] ABSTRACT

A medical forceps (10) for removal of tissue from the human or animal body, has two jaw parts at the end nearest the patient which can be moved relative to one another via grip elements at the end remote from the patient, said jaw parts having blades which coact in cutting fashion as said jaw parts are closed. There is releasably mountable on at least one of said jaw parts an adapter which has a blunt support surface, extending at least over a portion of said one jaw part on which it is mountable, which braces in planar fashion against said other jaw part as said jaw parts are closed when said adapter is mounted, so that said blades can no longer coact in cutting fashion as said jaw parts are closed. In a medical forceps whose jaw parts butt against one another in blunt fashion upon closing in order to grasp tissue, there is releasably mounted on at least one of said jaw parts an adapter which has an edge or a blade which, as said jaw parts are closed, coacts in cutting fashion with an edge of the other jaw part or with a blade of a second adapter releasably mounted on said other jaw part.

16 Claims, 6 Drawing Sheets

MEDICAL FORCEPS

This application is a continuation to pending International Application PCT/EP97/06215, filed Nov. 8, 1997, which designated the United States.

BACKGROUND OF THE INVENTION

The present invention relates to a medical forceps for removal of tissue from the human or animal body, having two jaw parts at the end nearest the patient which can be moved relative to one another via grip elements at the end remote from the patient, the jaw parts having blades which coact in cutting fashion as the jaw parts are closed.

The invention further relates to a medical forceps for removal of tissue from the human or animal body, having two jaw parts at the end nearest the patient which can be moved relative to one another via grip elements at the end remote from the patient, the jaw parts butting against one another in blunt fashion upon closing in order to grasp tissue.

Forceps of this kind of the first aforementioned type for detaching tissue, and forceps of this kind as cited secondly for grasping tissue, are commonly known.

In a surgical operation on the human or animal body, forceps for detaching tissue are used to detach or cut away tissue, for example organ or bone tissue. For this purpose, the forceps have at their end nearest the patient two jaw parts which have blades, i.e. sharpened regions with sharp cutting edges, which coact in order to detach the tissue.

There is known, for example, from the German brochure "Karl Storz Endoskope, Endoskopische Chirurgie" [Karl Storz endoscopes, endoscopic surgery], section 5, page SCT 5/4A (FRANGENHEIM forceps), a forceps referred to as "cut-through," the jaw parts of which have cutting edges in the longitudinal direction of the forceps or of the jaw parts, as well as front cutting edges running transverse to the longitudinal direction. "Cut-through" means that during cutting, a movable jaw part is moved through an immovable one, the blades moving past one another and detaching a piece of tissue grasped between them.

Also known, however, are forceps for the detachment of tissue which have only blades running in the longitudinal direction, which thus cut into the tissue in the manner of a scissors.

Also known are so-called "spoon forceps," whose two jaw parts each have a blade which butts against the other as the jaw parts are closed but do not move past one another, thus coacting in cutting fashion.

All the forceps of the afore-mentioned kinds can be used only to detach tissue. It is not possible with these forceps to grasp the detached tissue and remove it from the human body.

The forceps provided for removal of tissue samples are so-called grasping forceps, i.e. forceps of the type cited secondly above, the jaw parts of which are configured not as cutting tools but as grasping tools, which thus have surfaces that butt against one another in blunt fashion, and between which the detached tissue can be grasped without being cut in two.

In surgical operations in which pieces of tissue are to be removed, the surgeon is therefore compelled to use two forceps to detach and to remove the tissue, namely a cutting forceps and a grasping forceps. This has the disadvantage, however, that the surgeon must become familiar with the operation of two different forceps in order to acquire the operating confidence necessary in order to use them. Since, in addition, the tissue to be removed often cannot be detached with only a single cutting operation, the surgeon must switch forceps several times so as to remove from the body with the grasping forceps a piece of tissue initially detached with the cutting forceps. The result is that during a surgical procedure, the surgeon must repeatedly put down one forceps and pick up the respective other forceps.

A further disadvantage is the elevated cost of such known forceps, resulting from the fact that two complete forceps, one for detaching and one for grasping, must be made available with their shafts, actuation elements, and grip elements, although the cutting forceps and grasping forceps need to differ in functional terms only with regard to their jaw parts.

Since surgeons regard the switching of forceps as disadvantageous, they occasionally attempt to grasp the piece of tissue detached by the cutting forceps using the jaw parts of the cutting forceps; this entails the risk, however, that the piece of tissue being grasped will be separated into two parts as the forceps is being withdrawn, and the parts will remain in the body.

U.S. Pat. No. 4,711,240 furthermore discloses a surgical instrument with which tissue can be resected from soft, spongy organs, for example from the kidneys or the liver, without thereby damaging blood vessels present in those organs. For this purpose, the known instrument has at the end nearest the patient detachment tools configured in comb fashion which are closed toward one another, the blunt comb teeth engaging into one another and resecting the tissue from both sides of the organ. The comb-like detachment tools do not, however, coact in cutting fashion. Instead, when the detachment tools are closed, the tissue of the organ is crushed between the comb teeth and can then be flushed out. With this instrument it is not possible to grasp the resected tissue. An attachment having a smooth surface can be sticked on one of the two detachment tools and can then be used if tissue is to be resected from the organ from one side only, for example to remove kidney stones.

Also known, from EP-A-0 598 607, is a surgical forceps which is not cutting, but rather is used for atraumatic grasping of organs or blood vessels in order to move them aside so as to expose the operative area concealed behind them. For this purpose, the jaw parts are equipped with atraumatic, releasably mountable cushions, which do not traumatize or even damage the grasped organs or vessels when the jaw parts are closed. These known forceps cannot, however, be used as a cutting tool.

Even with the instruments cited above, there still exists the disadvantage that they have only one function, i.e. either only detaching tissue or only grasping tissue.

SUMMARY OF THE INVENTION

It is therefore the object of the invention to improve a medical forceps of the first kind cited initially, and a medical forceps of the kind secondly cited initially, in such a way that the operations of detaching and grasping or removing tissue can be performed successively, without requiring the surgeon for that purpose to put the forceps down and pick up another forceps.

According to the present invention, the object is achieved in terms of the forceps first cited initially in that there is releasably mountable on at least one of the jaw parts an adapter which has a blunt support surface, extending at least over a portion of the one jaw part on which it is mountable, which braces in planar fashion against the other jaw part as the jaw parts are closed when the adapter is mounted, so that the blades can no longer coact in cutting fashion as the jaw parts are closed.

According to the present invention, the object is achieved in terms of the forceps secondly cited initially in that there is releasably mountable on at least one of the jaw parts an adapter which has an edge or a blade which, as the jaw parts are closed, coacts in cutting fashion with an edge of the other jaw part or with a blade of a second adapter releasably mounted on the other jaw part.

The forceps according to the present invention differs from the known pure cutting forceps or pure grasping forceps in that if the jaw parts are configured as cutting tools, it can be used as grasping forceps after attachment of the adapter provided according to the present invention, and operates as a cutting forceps with the adapter removed; or, if the jaw parts of the forceps are configured as grasping tools, can operate as a cutting forceps after the adapter is attached. The forceps according to the invention thus alternately has the function of a cutting forceps and a grasping forceps.

If the jaw parts of the forceps according to the present invention are configured as cutting tools, when a tissue removal is performed the forceps according to the invention is first introduced with its jaw parts into the operative area without the adapter, in order to detach or cut through the tissue to be removed. Once the tissue piece has been detached, the forceps is withdrawn from the operative area. The adapter provided according to the present invention is then mounted on at least one of the jaw parts. The surgeon does not need to put the forceps down for this purpose, but rather can continue to hold the forceps in the same hand, and with the other hand can mount the adapter on the jaw part. For sterility reasons, this can also be done by a different person, so that the surgeon holds the forceps appropriately but does not release the forceps. Once the adapter has been mounted, the forceps can then be introduced with its jaw parts back into the operative area, so as then to grasp the detached tissue with the jaw parts that have been reconfigured by the adapter to function as grasping tools, and remove it from the operative area. Since the jaw parts are now functional purely as grasping tools, the surgeon does not need to carefully modulate his or her hand force, since there is no risk of cutting through the tissue piece being grasped.

In the case of a forceps of the kind, in which the jaw parts are configured as cutting tools, the advantage of the adapter is that the detached tissue can be securely grasped between the blunt support surface of the adapter and the other jaw part against which that support surface is braced, without thereby cutting it up. Since, when the adapter is mounted, the blades of the jaw parts do not come into effective engagement with one another when the jaw parts are closed if the adapter is mounted on the one jaw part, this eliminates the risk that the tissue will undesirably be cut in two by the sharp blades as it is being grasped.

Although disease phenomena are inherently similar, surgeons use different treatment methods and surgical techniques depending on the manifestation of the disease and on the patient. One example that could be mentioned is treatment of a cyst in the field of ear, nose and throat treatment. Sometimes a cyst is not completely removed, but rather is only cut, and the emerging fluid is aspirated away. A cutting tool is needed for this. In some cases the entire cyst is to be removed, which requires a grasping tool.

The invention now makes it possible to use both treatment methods or surgical methods with one and the same forceps, with the assistance of the adapter.

If the jaw parts of the forceps according to the invention are configured as grasping tools for grasping tissue, to detach the tissue first of all the at least one adapter is mounted on one of the jaw parts, thus reconfiguring the jaw parts to function as cutting tools. The adapter is then removed in order to take the tissue out. Since the operations of detaching and removing the tissue can be performed with one forceps, the surgeon needs to become accustomed to the movement characteristics of only a single forceps. The cost of the forceps according to the present invention is also advantageously reduced, since instead of two complete cutting and grasping forceps, only one forceps, with grip elements, shaft, and actuation elements, is necessary, while the adapter, as a simple additional element, can be manufactured much more economically than a second complete forceps.

In the context of the invention, provision can also be made to provide an adapter for both jaw parts.

The object is thus completely achieved.

In a further preferred embodiment of the forceps whose jaw parts have blades, the support surface extends over approximately the entire length of the blade of the one jaw part on which the adapter is mountable.

The advantage of this feature is that when the adapter is mounted, the piece of tissue can be grasped with the entire region of the jaw parts that acts in cutting fashion without the adapter.

It is further preferred in this context that when the adapter is mounted, the support surface projects out beyond the blade of the jaw part on which the adapter is mounted.

Advantageously, this feature reliably ensures that when the adapter is in the mounted state, the blades cannot come into effective engagement with one another as the jaw parts close. The tissue cannot be cut in two when grasped, since the support surface projecting out beyond the blade of the one jaw part is already coming into contact with the other jaw part before the two blades can come into effective engagement with one another.

In a preferred exemplifying embodiment, the one jaw part is movable and the other jaw part is immovable, the movable jaw part engaging into the immovable jaw part in order to detach the tissue, and the adapter being mountable on the movable jaw part.

With a configuration of this kind of the jaw parts of the forceps according to the present invention, which with this jaw part design is referred to as a cut-through forceps, the movable jaw part which engages into the immovable jaw part in order to detach the tissue is narrower in configuration than the immovable jaw part. The fact that the adapter is mountable on the narrower, movable jaw part results in the advantage that the total width of the forceps in the region of the jaw parts is not increased by the adapter, which is desirable particularly in the case of particularly narrow forceps that are used in operative areas which are extremely difficult of access. In the widely practiced minimally invasive surgical technique, the forceps can be moved in both functional states (i.e. with or without adapter) through one and the same endoscope or trocar.

It is preferred in this context if the movable jaw part is of concave configuration on a side facing the immovable jaw part.

The advantage of this feature is on the one hand that particularly sharp cutting edges can be configured at the peripheries of the movable jaw part, thus improving the function of the forceps according to the present invention for detaching the tissue; and on the other hand the detached tissue can be caught in the concavity as the piece of tissue is grasped, so that the function of the forceps according to the present invention as a grasping forceps is also thereby improved.

In a further preferred embodiment of the invention, the adapter has snap-lock means which can be snap-locked to corresponding snap-lock means of the one jaw part on which the adapter is mountable.

This advantageously creates an easily achievable and easily releasable joining capability between the adapter and the one jaw part, which on the one hand ensures reliable mounting of the adapter so that the latter does not undesirably detach from the jaw part in the operative area, and on the other hand allows easy and rapid handling when mounting and releasing the adapter.

In a further preferred embodiment of the invention, the adapter has a U-shaped body.

This embodiment has the advantage that the adapter can comfortably be held between two fingers of one hand, and can easily be slid or sticked with its open end onto a jaw part, thus further improving the handling of the forceps according to the present invention.

It is preferred in this context if two limbs of the U-shaped body are joined together by a web, such that when the adapter is mounted, the web fits around the jaw part on which the adapter is mountable.

The web advantageously prevents the two limbs of the U-shaped body from undesirably bending apart during mounting onto the one jaw part or, in the mounted state, while grasping or cutting the tissue. The adapter is thus highly stable, enhancing the operating reliability of the forceps according to the present invention.

In a further preferred embodiment of the invention, the jaw part on which the adapter is mountable has a circumferentially arranged groove, running in the longitudinal direction of the jaw part, into which corresponding projections of the adapter engage.

The advantage of this feature is that the adapter can always be positioned on the jaw part in the same position. The adapter is moreover secured, by the projections engaging into the groove, against undesired displacement perpendicular to the closing direction of the jaw parts as the jaw parts are closed in order to grasp or cut the piece of tissue.

In a further preferred embodiment, the adapter is made integrally of metal.

The integral configuration of the adapter makes possible economical manufacture of the adapter with a particularly simple design. Because the adapter is made of metal, it can be sterilized particularly easily, and can thus be used repeatedly.

Further advantages are evident from the description below of the appended drawings.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

Exemplifying embodiments of the invention are shown in the drawings and explained in more detail thereafter. In the drawings.

DETAILED DESCRIPTION OF PREFERRED EMBODIMENTS

Figure 1:
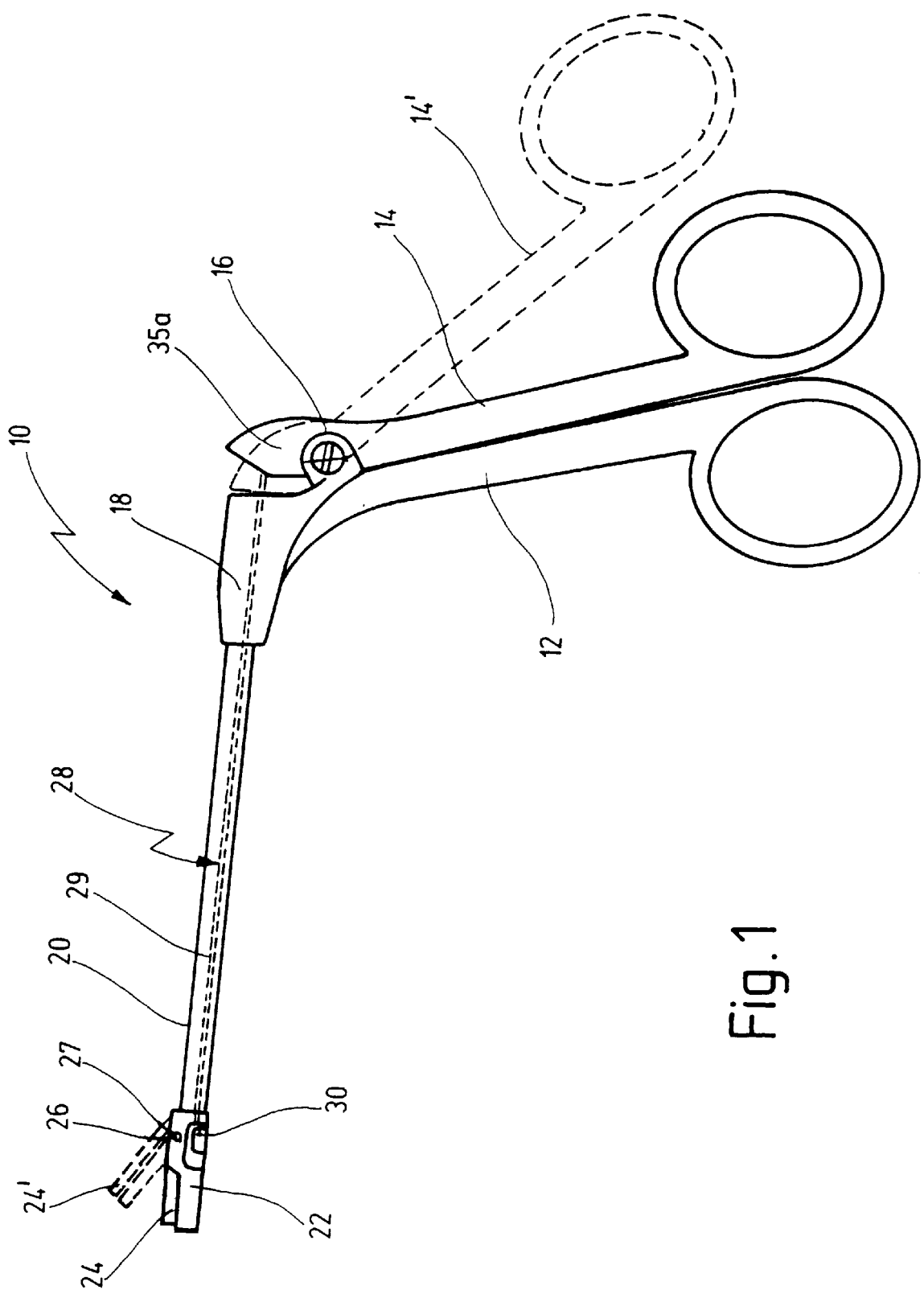
FIG. 1 shows a medical forceps in a side view.

FIG. 1 shows a medical forceps labeled in its entirety with the reference character 10. Forceps 10 is used to remove tissue from the human or animal body.

Provided at the end of forceps 10 remote from the patient are an immovable grip element 12 and a movable grip element 14, which are joined to one another via a hinge joint 16; movable grip element 14 is pivotable about hinge joint 16 constituting the rotation axis into an open position which is shown with dashed lines as 14'. An elongated tubular shaft 20 extends from an end region 18 of immovable grip element 12. Grip elements 12 and 14 as well as shaft 20 are manufactured from a metal or from a plastic having comparable properties.

An immovable jaw part 22 and a movable jaw part 24 are arranged at the end of shaft 20 nearest the patient. Immovable jaw part 22 is immovably joined to shaft 20. Movable jaw part 24 is pivotably mounted on immovable jaw part 22 via a pivot pin 26 constituting rotation axis 27.

Movable jaw part 24 is joined non-positively to movable grip element 14 via an actuation element 28. Actuation element 28 has a wire member 29 which has at its end nearest the patient a pin 30 which extends perpendicular to wire member 29. Pin 30 is machined, together with wire member 29, from a solid material, specifically from a hardened steel.

Pin 30 engages into a corresponding recess 32 (see FIG. 2) of movable jaw part 24, recess 32 being arranged in a widened solid section 33 (see FIG. 9) of movable jaw part 24 which is received in a recess 35 (see FIG. 2) of immovable jaw part 22. Actuation element 28 extends, proceeding from movable jaw part 24, in shaft 20 through end region 18 of immovable grip element 12 to an end region 35a of movable grip element 14, where it is attached via attachment means (not shown here). As grip elements 12, 14 are closed (dashed-line position), the opened jaw part 24 (dashed-line position) moves toward immovable jaw part 22 and passes through it.

Figure 2:
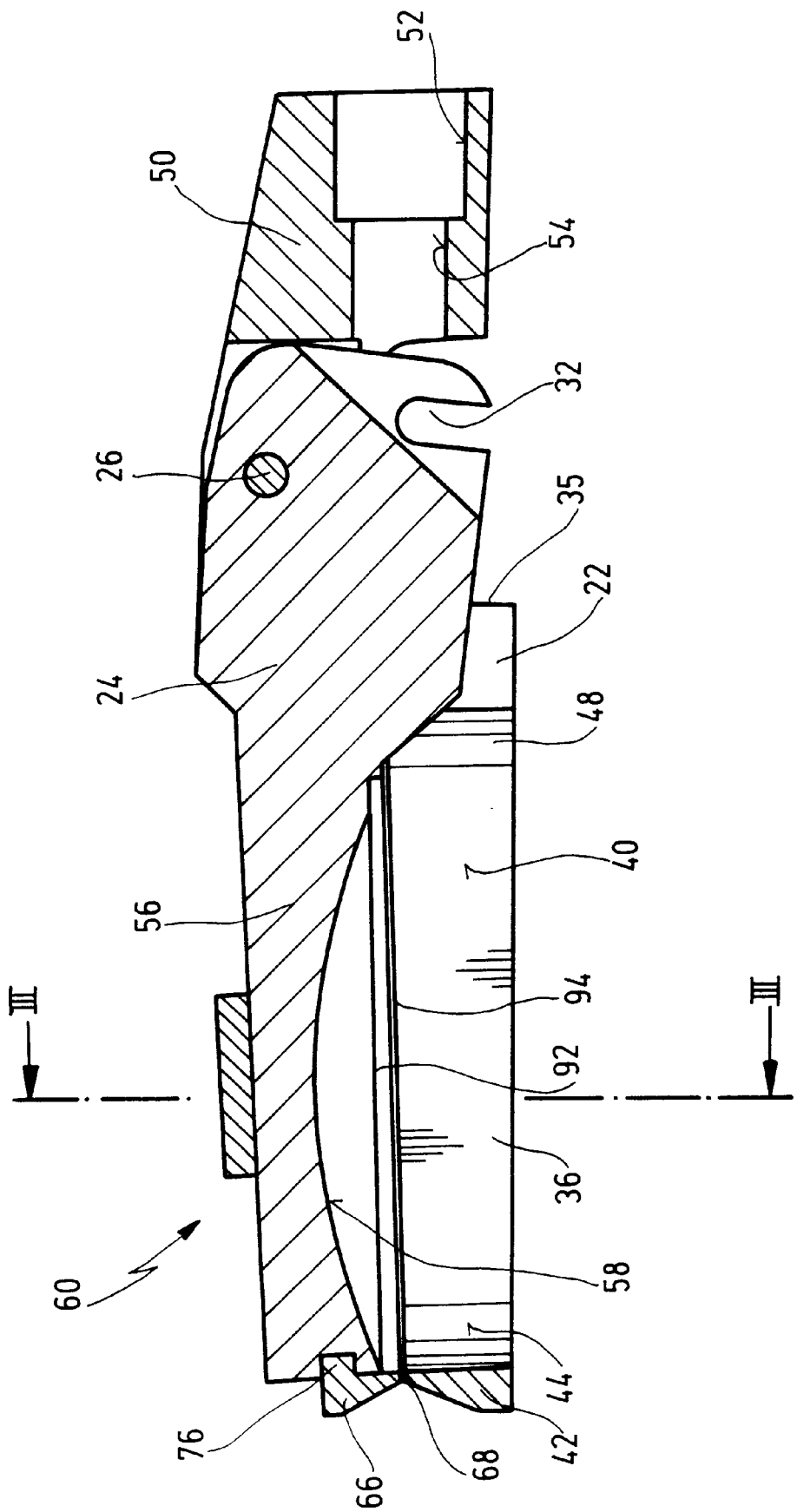
FIG. 2 shows a section through the longitudinal center plane of the two jaw parts, configured as cutting tools, of the medical forceps of FIG. 1 at enlarged scale, an adapter being placed onto one jaw part.
Figure 3:
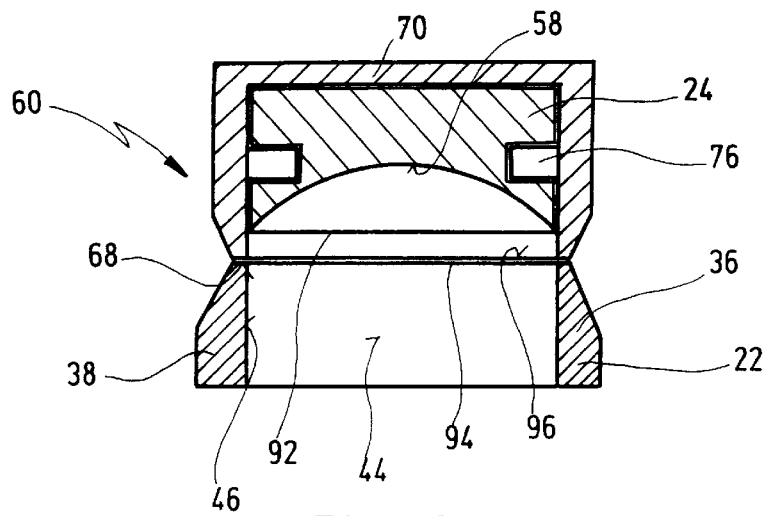
FIG. 3 shows a section through the jaw parts along line III—III of FIG. 2.
Figure 4:
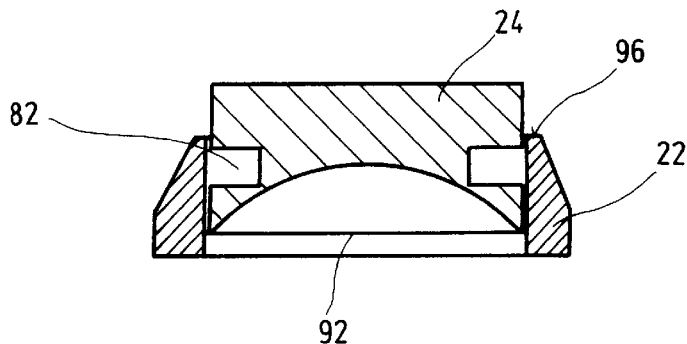
FIG. 4 shows a section corresponding to FIG. 3 through the two jaw parts without an adapter.
Figure 5:
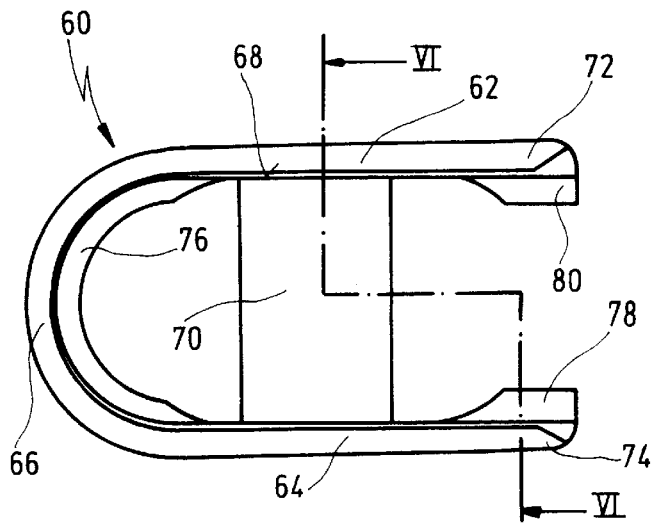
FIG. 5 shows a bottom view of the adapter.
Figure 6:
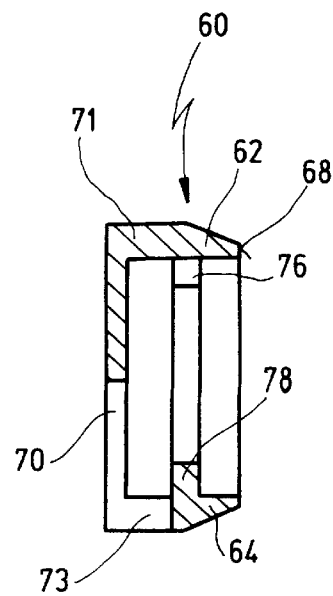
FIG. 6 shows a section through the adapter along line VI—VI of FIG. 5.
Figure 7:
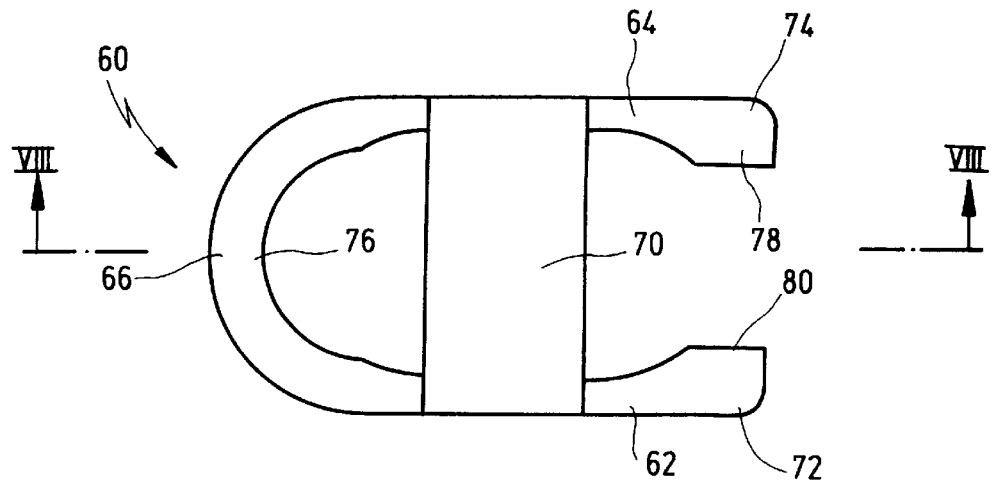
FIG. 7 shows a plan view of the adapter.
Figure 8:
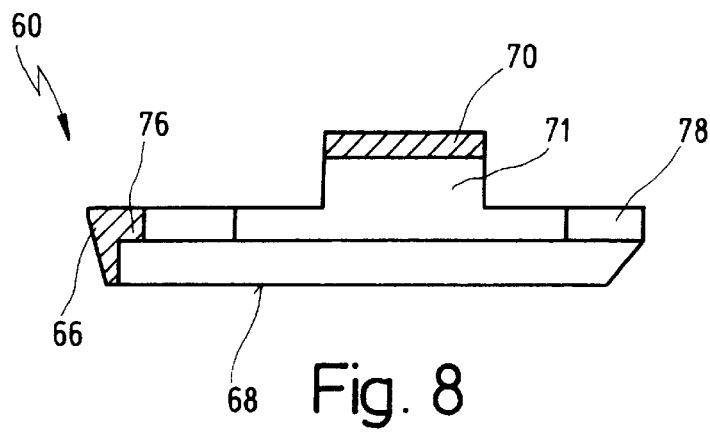
FIG. 8 shows a section through the adapter along line VIII—VIII of FIG. 7.

FIGS. 2 through 4 depict jaw parts 22 and 24 of medical forceps 10 at enlarged scale. Immovable jaw part 22 is constituted from two lateral limbs 36 and 38 running approximately parallel to one another, a smooth linear inner wall 40 of the right-hand limb 36 (looking toward the end nearest the patient) being visible in the sectioned representation of FIG. 2.

At the end nearest the patient, limbs 36 and 38 come together in approximately semicircular shape to form a vertex section 42. Inner wall 40 of limb 36 thus transits continuously via a semicircularly curved inner wall 44 into an inner wall 46, once again running linearly, of limb 38. Inner walls 40, 44 and 46 are of linear configuration in the vertical direction, so that a substantially U-shaped open space is formed between limbs 36 and 38 in the region nearest the patient.

In a center section 48, limb 36 is curved inward; the same applies to limb 38, but limbs 36 and 38 are not joined to one another there. Only at the outer end remote from the patient are limbs 36 and 38 joined integrally to one another by an end section 50. The region between inner walls 40, 44, and 46 is continuously open in the vertical direction.

Provided in end section 50 is a bore 52 with which immovable jaw part 22 can be placed onto shaft 20 and attached securely to the shaft, for example by soldering. Bore 52 continues into a further, smaller-diameter bore 54, which is provided for the passage of actuation element 28 which can be attached in lossproof fashion to pin 30 in recess 32 of immovable jaw part 24.

Movable jaw part 24 is arranged between limbs 36 and 38 of immovable jaw part 22, and is configured as a solid member whose peripheral contour in a region 56 nearest to the patient of jaw part 24 corresponds to the contour determined by inner walls 40, 44, and 46 of immovable jaw part 22.

A lower surface 58 of movable jaw part 24, facing immovable jaw part 22, is of concave configuration.

In FIGS. 2 and 3, there is mounted on medical forceps 10, and more precisely on movable jaw part 24, an adapter generally designated 60, by way of which forceps 10 operates as a grasping forceps, as shown in FIG. 3. Without adapter 60, forceps 10 operates as a cutting forceps, as shown in FIG. 4. It is evident from this that without adapter 60, movable jaw part 24 can pass through immovable jaw part 22, and forceps 10 thus operates as a cut-through forceps.

Adapter 60 is releasably mountable on movable jaw part 24, i.e. adapter 60 can be placed on movable jaw part 24 and removed again therefrom.

Before the function of adapter 60 in coaction with jaw parts 22 and 24 is discussed, the configuration of adapter 60 will first be described in more detail with reference to FIGS. 5 through 8.

Adapter 60 is configured overall as a metal U-shaped body having two limbs 62 and 64 which are integrally joined to one another via a section 66 of approximately semicircular configuration. Limbs 62 and 64 taper on one side in a wedge shape, toward the underside (FIGS. 5 and 6) of adapter 60, to a narrow support surface 68 which runs over the entire body of adapter 60 on the underside of adapter 60, also in a U-shape.

On the upper side (FIG. 7) of adapter 60, a web 70 in the form of a flat rectangular plate joins the two limbs 62 and 64 integrally to one another via vertical sidewalls 71 and 73, while free ends 72 and 74 of limbs 62 and 64 are not joined, so that they are elastically bendable.

In addition, the semicircular section 66 of adapter 60 has an inwardly directed projection 76 that is also semicircularly curved.

Free ends 72 and 74 are equipped with snap-lock means 78 and 80, also in the form of inwardly directed projections, which extend over a portion of free ends 72 and 74 of limbs 62 and 64 and lie in the same plane as semicircular projection 76.

Figure 9:
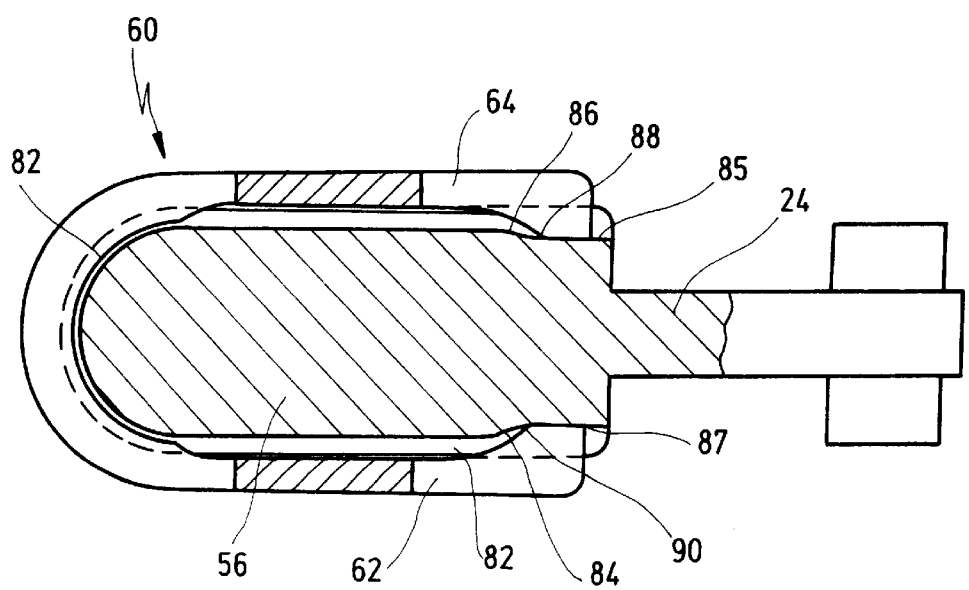
FIG. 9 shows a partially sectioned plan view of the movable jaw part with the adapter mounted thereon.

In FIG. 9, adapter 60 is shown mounted on movable jaw part 24.

Adapter 60 is placed or slid onto movable jaw part 24 from the end nearest the patient; snap-lock means 78 and 80 in the form of projections, and projection 76, thereby engage into a groove 82, recessed into movable jaw part 24, which is arranged approximately centeredly in terms of the height of movable jaw part 24 and extends peripherally in a U-shape around the entire region 56 nearest the patient of movable jaw part 24. In the mounted state, web 70 fits around movable jaw part 24 on its upper side, as is evident from FIG. 3.

Sections 85 and 87, more remote from the patient, of groove 82 are cut somewhat more deeply into movable jaw part 24, and transit via beveled regions 84 and 86 into the remaining portion of groove 82. The ends of regions 84 and 86 more remote from the patient constitute snap-lock means 88 and 90 of movable jaw part 24.

In order to place or slide adapter 60 onto movable jaw part 24, its free ends 72 and 74 are inserted with projections 78 and 80, from the end of movable jaw part 24 nearest the patient, into groove 82. Adapter 60 is then slid toward the end of movable jaw part 24 remote from the patient until projections 78 and 80 of adapter 60 have moved past beveled regions 84 and 86 and come to rest in sections 85 and 87 of groove 82. In this state, the beveled regions constitute catches preventing the adapter from being pulled out, so the latter is thus snap-locked. Snap-locking is accomplished by the fact that free ends 72 and 74 of adapter 60 are initially somewhat spread apart when slid into groove 82, and after passing over beveled regions 84 and 86, come to rest in sections 85 and 87 of groove 82, which are cut in more deeply. To remove adapter 60, the latter is pulled off from jaw part 24 toward the end of jaw part 24 nearest the patient.

The operation of medical forceps as a cutting and grasping forceps will be explained below with reference to FIGS. 3 and 4.

FIG. 4 illustrates the case in which forceps 4 is used as a cutting forceps to detach tissue. In this case, jaw parts 22 and 24 coact as cutting tools.

For this purpose, movable jaw part 24 has on its lower side, i.e. the side facing immovable jaw part 22, a U-shaped blade 92 in the form of a sharp edge, which coacts with a corresponding blade 94 of immovable jaw part 22 that is constituted by the upper edge of inner walls 40, 44, and 46 of immovable jaw part 22. Blades 92 and 94 extend in a U-shape, corresponding to the configuration of jaw parts 22 and 24. In order to detach or cut through tissue, jaw parts 22 and 24 are closed via grip elements 12 and 14 so that upon closing, movable jaw part 24 engages into immovable jaw part 22, blades 92 and 94 being guided past one another and thus achieving the cutting effect. When jaw parts 22, 24 are configured in this fashion, forceps 10 is referred to as a "cut-through" forceps.

FIG. 3, on the other hand, shows the case in which forceps 10 operates as a grasping forceps because adapter 60 has been mounted on movable jaw part 24. Adapter 60 is configured, in terms of immovable jaw part 24, in such a way that its support surface 68 overlaps blade 92 of movable jaw part 24 in the direction of immovable jaw part 22. Support surface 68 extends over approximately the entire length of blade 92 of movable jaw part 24, so that when adapter 60 is mounted, the entire cutting region of jaw parts 22 and 24 is utilized as an effective region for grasping. When jaw parts 22 and 24 are closed, support surface 68 then butts in planar, i.e. blunt, fashion against a periphery 96 also configured in planar fashion as a support surface on the upper side, i.e. the side facing movable jaw part 24, of immovable jaw part 22, without allowing blades 92 and 94 to come into effective engagement with one another. With jaw parts 22 and 24 in the closed position, blades 92 and 94 are spaced apart from one another. FIG. 3 already shows the maximally closed position of jaw parts 22 and 24 when adapter 60 is mounted on movable jaw part 24.

The previously detached tissue can then be grasped between support surface 68 of adapter 60 and periphery 96 of immovable jaw part 22 and retained securely for removal from the body, without thereby being cut in two.

In the exemplary embodiment of FIG. 3, limbs 36 and 38 of immovable jaw part 22 taper in wedge form on their exterior toward periphery 96, while limbs 62 and 64 of adapter 60, as already mentioned, taper on their exterior toward support surface 68.

Figure 10:
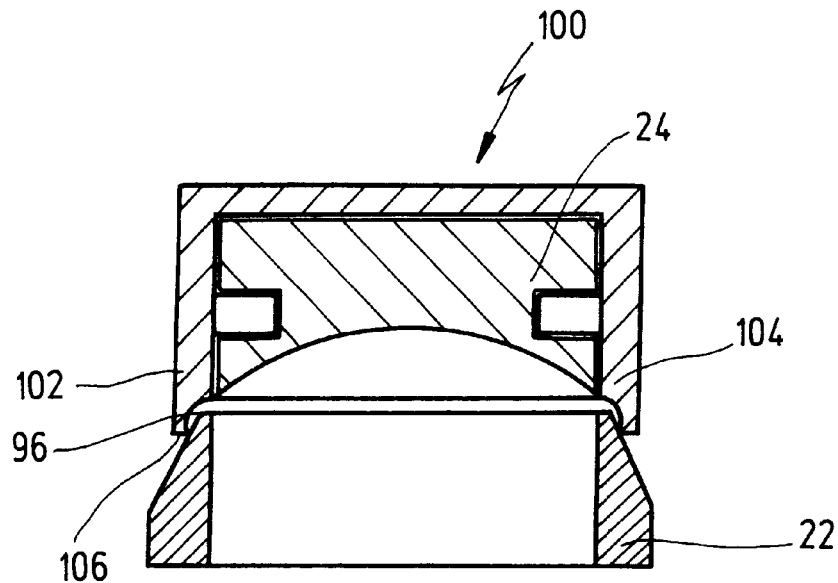
FIG. 10 shows a further exemplifying embodiment of the invention in a section corresponding to FIG. 3.

FIG. 10 shows, as a further exemplifying embodiment, an adapter 100 which is modified with respect to adapter 60 and is releasably mountable on movable jaw part 24 (which is of unchanged configuration). Limbs 102 and 104 of adapter 100 have a lower support surface 106 which is not braced against periphery 96 of immovable jaw part 22 but rather fits around periphery 96 and braces against the beveled sides of jaw part 22. A larger grasping surface is thereby created.

Figure 11:
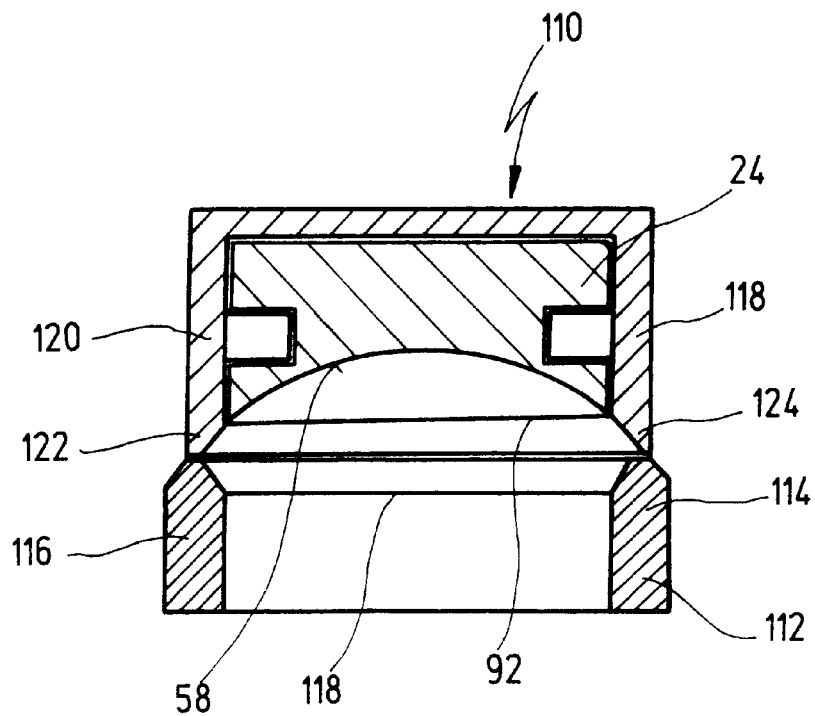
FIG. 11 shows a further exemplifying embodiment of the invention in a section also corresponding to FIG. 3.

FIG. 11 shows a further exemplifying embodiment of the invention in which an adapter 110 and an immovable jaw part 112 are of modified configuration as compared with adapter 60 and immovable jaw part 22 of FIGS. 1 through 9.

Immovable jaw part 112 has limbs 114 and 116 which are configured in internally beveled fashion on their upper side facing movable jaw part 24, so that a peripheral edge 118 constitutes a cutting edge of immovable jaw part 112 which coacts with cutting edge 92 of movable jaw part 24.

Adapter 110 has limbs 118 and 120 which are internally curved, corresponding to the curvature of internal surface 58 of movable jaw part 24, at ends 122 and 124 facing immovable jaw part 112. This creates a relatively small grasping surface with which, for example, a cyst can be grasped and then broken off.

Figure 12:
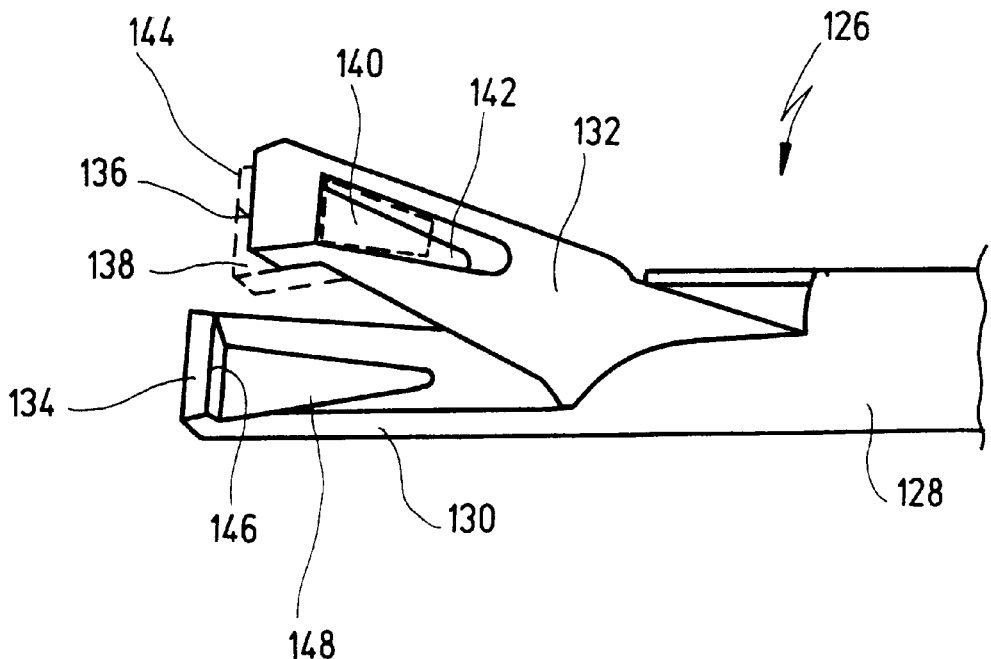
FIG. 12 shows an exemplifying embodiment of a forceps whose jaw parts are configured as grasping tools.

According to a further exemplifying embodiment, FIG. 12 shows the end nearest the patient of a medical forceps 126 having a shaft 128 at whose end nearest the patient two jaw parts 130 and 132, configured as grasping tools, are mounted, and are movable relative to one another via grip elements (not shown here) at the end of forceps 126 remote from the patient, jaw part 130 being shaft-mounted and jaw part 132 being movable. Jaw parts 130 and 132 have at their ends nearest the patient surfaces 134 and 136 which butt in planar fashion against one another upon closing, so that upon closing, jaw parts 130 and can grasp tissue that has already been detached, without cutting it in two.

An adapter 138 shown with dashed lines, which is releasably mountable on jaw part 132, is provided for movable jaw part 132.

For this purpose, adapter 138 has a section 140 which can be snapped into a window 142 provided in jaw part 132, for example via a system of grooves and projections (not shown here), so that adapter 138 is held on jaw part 132 in lossproof fashion.

Adapter 138 has an edge 144 which protrudes beyond surface 136 of jaw part 132 and is arranged behind the latter when viewed from the end nearest the patient, so that when jaw parts 130 and 132 are closed, it coacts in cutting fashion with an edge 146 of immovable jaw part 130 to detach tissue. As jaw parts 130 and 132 are closed, adapter 138 engages into a window 148 of immovable jaw part 130 in such a way that when adapter 138 is mounted, jaw parts 130 and 132 coact as cut-through cutting tools.

Figure 13:
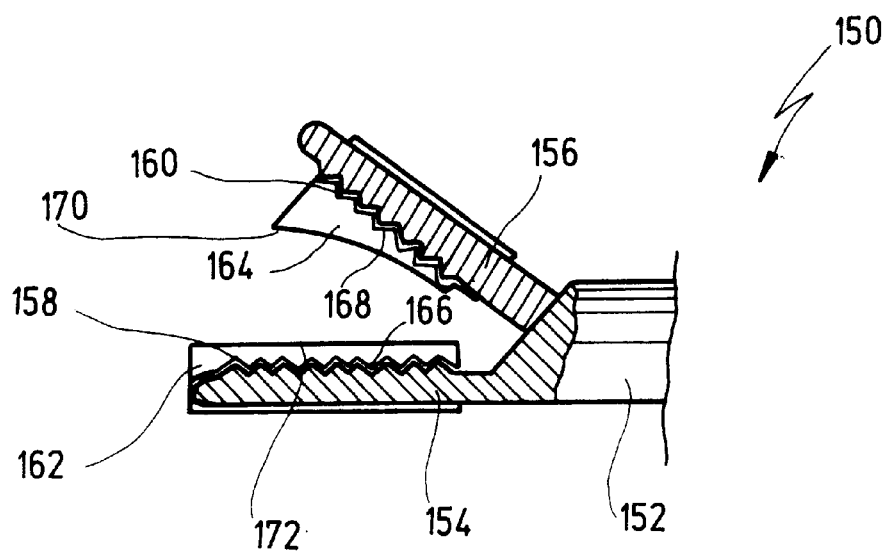
FIG. 13 shows a further exemplifying embodiment of a forceps whose jaw parts are configured as grasping tools.

Lastly, FIG. 13 shows the end nearest the patient of a forceps 150 which has a shaft 152 on whose end nearest the patent a immovable jaw part 154 and a movable jaw part 156 are arranged.

Jaw parts 154 and 156 are configured as grasping tools; specifically, jaw parts 154 and 156 have tooth sets 158 and 160 which engage into one another as jaw parts 154 and 156 close, and between which a previously detached piece of tissue can be grasped. An adapter 162 releasably mountable onto jaw part 154 is provided therefor, and an adapter 164 releasably mountable onto jaw part 156 is provided therefor. For lossproof attachment of adapters 162 and 164, the latter have corresponding tooth sets 166 and 168 which, when adapters 162 and 164 are put in place, engage into tooth sets 158 and 160 of jaw parts 154 and 156 and are thus snap-locked thereto. Adapter 164 has a blade 170 which, with adapter 164 in the mounted state, is ar ranged laterally on movable jaw part 156. As jaw parts 154 and 156 close, blade 170 coacts in cutting fashion, specifically in the manner of a scissors, with an outer edge 172 of adapter 162 in order to detach tissue.

What is claimed is:

1. A medical forceps for removal of tissue from the human or animal body, comprising:

a grip having two grip elements movable relative to each other, a shaft connected to said grip, two jaw parts disposed at said shaft at an end nearest the patient thereof and movable relative to each other, said two jaw parts having blades which coact in cutting fashion as said jaw parts are closed against each other, wherein an adapter is releasably mountable on at least one of said jaw parts, said adapter having a blunt support surface extending at least over a portion of said one jaw part on which it is mountable, which braces in planar fashion against said other jaw part as said jaw parts are closed when said adapter is mounted, so that said blades can no longer coact in cutting fashion as said jaw parts are closed.

2. The forceps of claim 1, wherein said support surface extends over approximately the entire length of said blade of said one jaw part on which said adapter is mountable.

3. The forceps of claim 1, wherein, when said adapter is mounted, said support surface projects out beyond said blade of said jaw part on which said adapter is mountable.

4. The forceps of claim 1, wherein one of said jaw parts is movable and the other of said jaw parts is immovable, said movable jaw part engaging into said immovable jaw part in order to detach the tissue, and wherein said adapter is mountable on said movable jaw part.

5. The forceps of claim 4, wherein said movable jaw part is of concave configuration on a side facing said immovable jaw part.

6. The forceps of claim 1, wherein said adapter has snap-lock means which can be snap-locked to corresponding snap-lock means of said one jaw part on which said adapter is mountable.

7. The forceps of claim 1, wherein said adapter has a U-shaped body.

8. The forceps of claim 7, wherein two limbs of said U-shaped body are joined together by a web, such that when said adapter is mounted, said web fits around said jaw part on which said adapter is mounted.

9. The forceps of claim 1, wherein said jaw part on which said adapter is mountable has a circumferentially arranged groove, running in the longitudinal direction of said jaw part, into which corresponding projections of said adapter engage.

10. The forceps of claim 1, wherein said adapter is made integrally of metal.

11. A medical forceps for removal of tissue from the human or animal body, comprising:
- a grip having two grip elements movable relative to each other,
- a shaft connected to said grip,
- two jaw parts disposed at said shaft at an end nearest the patient thereof and movable relative to each other,
- said two jaw parts butting against one another in blunt fashion upon closing in order to grasp tissue,
- wherein an adapter is releasably mountable on at least one of said jaw parts which has an edge or a blade which, as said jaw parts are closed, coacts in cutting fashion with an edge of said other jaw part or with a blade of a second adapter releasably mounted on said other jaw part.

12. The forceps of claims 11, wherein said adapter has snap-lock means which can be snap-locked to corresponding snap-lock means of said one jaw part on which said adapter is mountable.

13. The forceps of claim 11, wherein said adapter has a U-shaped body.

14. The forceps of claim 13, wherein two limbs of said U-shaped body are joined together by a web, such that when said adapter is mounted, said web fits around said jaw part on which said adapter is mounted.

15. The forceps of claims 11, wherein said jaw part on which said adapter is mountable has a circumferentially arranged groove, running in the longitudinal direction of said jaw part, into which corresponding projections of said adapter engage.

16. The forceps of claim 11, wherein said adapter is made integrally of metal.

* * * * *